United States Patent [19]

Ogi et al.

[11] Patent Number: 5,696,384
[45] Date of Patent: Dec. 9, 1997

[54] COMPOSITION FOR FORMATION OF ELECTRODE PATTERN

[75] Inventors: Katsumi Ogi; Hiroto Uchida; Atsushi Itsuki, all of Omiya, Japan

[73] Assignee: Mitsubishi Materials Corporation, Tokyo, Japan

[21] Appl. No.: 579,413

[22] Filed: Dec. 27, 1995

[30] Foreign Application Priority Data

Dec. 27, 1994 [JP] Japan .................. HEI6-324875
Apr. 7, 1995 [JP] Japan .................. HEI7-082546
Jul. 4, 1995 [JP] Japan .................. HEI7-168661

[51] Int. Cl.[6] .................................................. C09K 3/00
[52] U.S. Cl. .................... 252/182.12; 252/182.3
[58] Field of Search ................... 252/182.12, 182.3

[56] References Cited

U.S. PATENT DOCUMENTS

| | | | |
|---|---|---|---|
| 3,867,343 | 2/1975 | Garden | 502/150 |
| 4,472,517 | 9/1984 | Tsao et al. | 502/62 |
| 4,764,357 | 8/1988 | Sherif et al. | 252/182.12 |
| 5,252,247 | 10/1993 | Greco et al. | 252/182.12 |
| 5,292,594 | 3/1994 | Liburdi et al. | 428/650 |
| 5,410,007 | 4/1995 | Lewis et al. | 502/158 |

OTHER PUBLICATIONS

Appleton et al., Chem. Abs., 106, abs. #84805 (1986).

Primary Examiner—Edward A. Miller
Attorney, Agent, or Firm—Oblon, Spivak, McClelland, Maier & Neustadt, P.C.

[57] ABSTRACT

A Pt film-forming composition comprises a dimethyl Pt(II) (N,N,N',N'-tetramethylethylenediamine) complex and an organic solvent. A Pt film is formed by applying this composition to a substrate and then subjecting the applied layer of the composition to a heat treatment. A Pt film pattern is obtained by applying this composition to a substrate, pattern-exposing the produced applied layer of the composition to radiation, developing the exposed layer, and then subjecting the developed layer to a heat treatment.

2 Claims, 2 Drawing Sheets

COMPOSITION FOR FORMATION OF ELECTRODE PATTERN

BACKGROUND OF THE INVENTION

1. Field of the Invention

The present invention relates to a Pt film-forming composition, to a Pt film and to a Pt film pattern formed of the composition; to an Ir film and to an Ir oxide film-forming composition and to an Ir film, to an Ir oxide film, to an Ir film pattern, and to an Ir oxide film pattern formed of the composition; and to a method for forming a platinum film.

2. Description of the Background

As a way of forming a thin film of Pt such as contacts and wires in a semiconductor device, a method in which a coating solution of a Pt film-forming composition containing an organic compound is applied to a substrate and then heat-treating the applied layer of the solution, is most convenient and commercially advantageous. Normally, a MO (metallo-organics) paste formed of an organic acid salt or a thiolate compound of Pt is used as the Pt film-forming composition.

Since the conventional Pt film-forming composition must be fired at a high temperature in the range of 500° to 800° C., the formation of a Pt film on a substrate material of a resin such as a polyimide, which requires the use of low temperatures of not higher than 300° C. for film formation and the application of a Pt film to the process of using a Si semiconductor or such compound semiconductor materials as GaAs, InP, and GaN, have been found difficult to accomplish.

For electrode materials, which only sparingly encounter fatigue because of polarization inversion, which poses a problem of quality for a nonvolatile memory utilizing the polarization inversion of such a ferroelectric substance as PZT, for example, Ir films and Ir oxide films exhibit excellent properties.

The method for forming Ir films and the Ir oxide films normally involves applying to a substrate a coating solution of an Ir film-forming composition containing an organic Ir compound, and then heat-treating the applied layer of the solution. This method is most convenient and commercially advantageous. Normally, a MO (metallo-organics) paste of an organic acid salt of Ir, specifically iridium octylate, is used.

Since the conventional Ir film-forming composition mentioned above must be fired at a high temperature in the range of 500° to 800° C., the formation of an Ir film on a material of a resin such as polyimide, which demands use of a low temperature of not higher than 300° C. for film formation and the application of an Ir film in the process of using a Si semiconductor or such compound semiconductor materials as GaAs, InP, and GaN, has been found difficult to accomplish. Usually, therefore, a Pt or Ir circuit pattern is formed by the complicated technique of forming a Pt film or an Ir film by a vacuum deposition process or by a sputtering process and then subjecting the Pt film or the Ir film to dry etching such as by ECR (Electron Cyclotron Resonance) plasma, for example.

In the formation of a Pt circuit pattern or an Ir or an Ir oxide electrode, when an Ir film or an Ir oxide film having a smooth surface and a low resistance is manufactured by applying a coating solution or a Pt film or an ir film-forming composition containing an organic Pt compound or an organic Ir compound on a substrate by spin coating, spray coating, dip coating, or screen printing technique and then subjecting the applied solution to a heat treatment at a relatively low temperature, the process for the formation of the Pt film or the Ir or the Ir oxide film can be simplified to a notable extent.

When this composition is exposed to radiation such as light, laser radiation, electron beams, or X-rays, thereby precipitating Pt or Ir, the pattern of a Pt film or an Ir film or an Ir oxide film can be easily formed on a substrate by exposing the applied layer of the composition to the radiation, which decomposition occurs easily, washing and removing the unexposed part of the layer with a solvent, and then subjecting the resultant etched layer to a heat treatment. Specifically, in this case, where a master circuit pattern is inscribed on a substrate by the action of a scanning laser or by the transfer of a master pattern, the circuit pattern of a Pt film or an Ir film or an Ir oxide film, which does not easily etch, can be formed directly on the substrate. Thus, this process of pattern formation is limited in its effectiveness.

In order to form various platinum films such as the undercoating electrode of a dielectric memory in a semiconductor device, a vacuum deposition method, a sputtering method, a metalorganic chemical vapor deposition (hereinafter abbreviated as "MOCVD") method, or the like, all of which methods are known, can be used. The starting material for preparation of the platinum film is usually cyclopentadienyl trimethylplatinum (IV), $(C_5H_5)Pt(CH_3)_3$, (hereinafter abbreviated as "(Cp)PtTM"), particularly when the MOCVD method is used.

Figure 3:
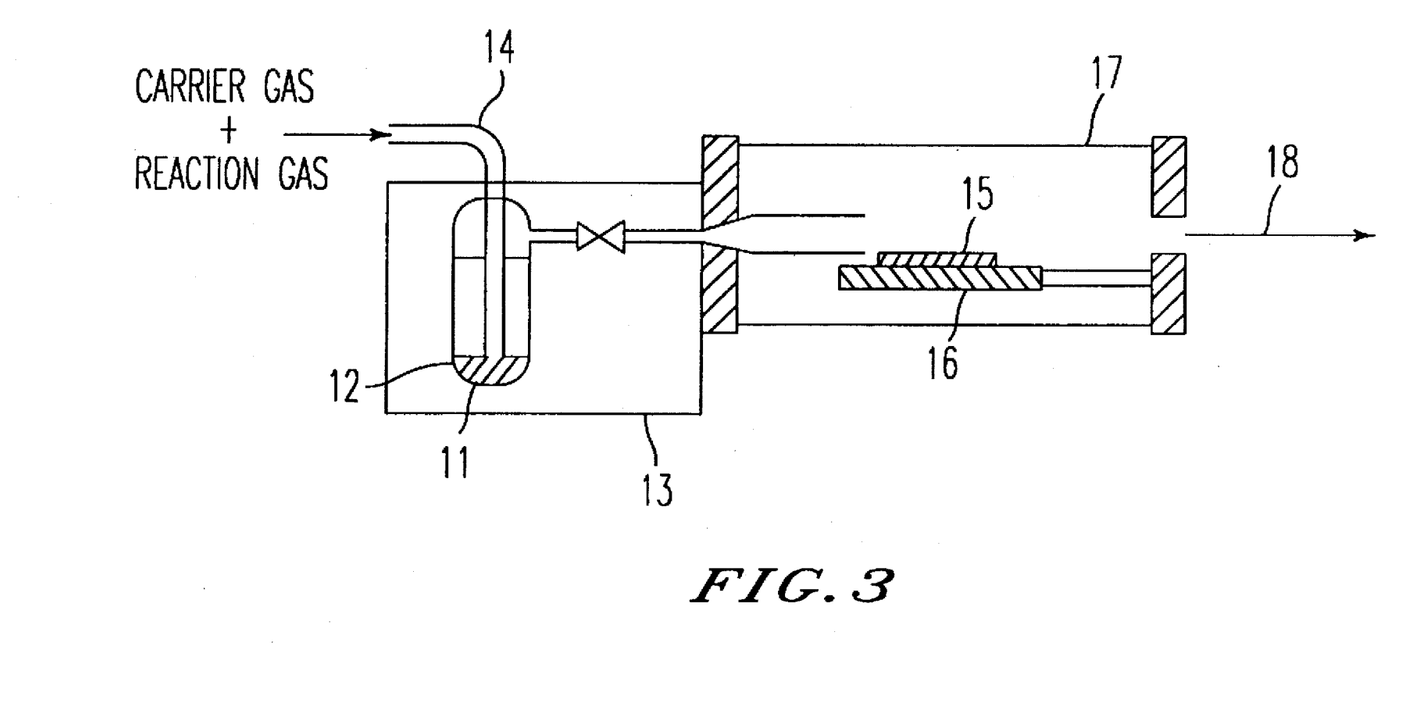
FIG. 3 shows an apparatus which effects thermal decomposition by the MOCVD method.

The formation of a platinum film by the MOCVD method using the above Pt compound can be achieved by a procedure which, as shown in the schematic explanatory diagram of FIG. 3, comprises placing a substrate 15 on a heater 16 provided in a reaction furnace 17, meanwhile vaporizing, in a heating furnace 13 disposed in connection with the reaction furnace 17, a raw material 11 for vapor deposition, which is the above-mentioned organic platinum compound which is placed in a vaporizer 12, thereby causing the resultant vapor to be conveyed to and pass into the reaction furnace 17 as it is entrained by a carrier gas such as Ar and a reaction gas such as $H_2$ introduced via a pipe 14, and inducing precipitation of platinum on the substrate 15 which is heated. In the drawing, 18 strands for a vacuum suction pipe. This procedure is called a thermal decomposition type MOCVD method.

During film formation by the MOCVD method, cyclopentadienyl trimethylplatinum adheres to the substrate by reaction with hydroxyl groups on the substrate.

By using a conventional method for the formation of a platinum film such as the vacuum deposition method, which includes the MOCVD method and the sputtering method, it is difficult to attain direct formation of a patterned platinum film on a substrate. Thus, a platinum film which is normally applied to a semiconductor device, is formed by dry-etching the platinum film formed on the substrate in such a manner as to provide a predetermined pattern (JP-A-60-243,284 and JP-A-05-175,174).

The conventional MOCVD method, which results in the adhesion of a platinum compound to a substrate through the medium of hydroxyl groups on the substrate, has the disadvantage that the platinum compound exhibits poor adhesiveness to the substrate and consequently the produced platinum film suffers poor adhesive strength.

Further, since the conventional methods have difficulty in directly forming a patterned platinum film on a substrate, a fine work by dry etching of the platinum film is required and this complicates the process. Moreover, since the fine work of the platinum film by etching is difficult, a problem which occurs is that it permits no easy patterning of the platinum film, and therefore it is quite possible to inflict damage to dielectric films of PZT, BST, and the like interposed between the platinum films during the course of work.

Particularly in recent years, a trend has developed for semiconductor devices having increasingly higher degrees of integration, with a concomitant need for platinum films of decreasing thickness. This need or requirement has increased the difficulty of controlling the uniformity and fine work of platinum films during production.

SUMMARY OF THE INVENTION

Accordingly, one object of the present invention is to provide a Pt film-forming composition which exhibits outstanding stability of preservation of heat and coating properties, and which provides a Pt film having a low resistance and smooth surface, which is formed easily by a heat treatment performed at a relatively low temperature, the composition permitting a patterned Pt film to be easily formed on a substrate by a procedure of exposing the composition to radiation, development, and heat treatment, and also providing a Pt film and a Pt film pattern formed from the composition.

Another object of the present invention is to provide an Ir film or an Ir oxide film-forming composition which exhibits outstanding preservation of heat and coating properties which allows an Ir film or an Ir oxide film having a low resistance and smooth surface to be formed easily by a heat treatment performed at a relatively low temperature, and permits a patterned Ir film or Ir oxide film on a substrate to be easily formed by a procedure comprising exposure to radiation, development, and heat treatment, and further an Ir film, an Ir oxide film, and an Ir film pattern, and an Ir oxide film pattern formed from the composition.

Yet another object of the present invention is to provide a MOCVD method such as a thermal decomposition MOCVD method of producing a platinum film which is superior to the platinum film which is formed by sputtering with respect to flatness and adhesiveness to a substrate to be formed as directly patterned on a substrate.

Briefly, this object and other objects of the present invention, as hereinafter will become more readily apparent can be attained by:

(1) A Pt film-forming composition of dimethyl Pt(II)(N, N,N',N'-tetramethylene diamine) in an organic solvent;

(2) A method of forming a Pt film on a substrate by applying a film-forming Pt composition of the invention on a substrate and then heat treating the applied layer;

(3) A method of forming a Pt film on a substrate by pattern-exposing an applied layer of the composition to radiation, removing (by washing) unexposed composition and then heating the developed applied layer;

(4) An Ir film, Ir oxide film-forming composition of an Ir (I) cyclopentadienyl complex in a solvent;

(5) A method of forming an Ir or Ir oxide film by applying the above Ir composition as a layer to a substrate and then heating the applied layer in a hydrogen or oxidizing atmosphere;

(6) A method of forming an Ir or IrO film by pattern-exposing an applied layer of the Ir composition on a substrate to radiation, removing (by washing) unexposed applied layer material with a solvent and then heating the developed layer in a reducing or oxidizing atmosphere; and (7) A method of forming a Pt film on a substrate by deposition an organoplatinum complex on an electroconductive layer which covers at least a portion of said substrate.

BRIEF DESCRIPTION OF THE DRAWINGS

A greater understanding of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The Pt film-forming composition is a dimethyl Pt (II) (N,N,N',N'-tetramethylethylenediamine) complex (hereinafter "DMPt(II)TMEDA"), which has the following structural formula (1), and an organic solvent.

The Pt film of the present invention is formed on a substrate by the steps of applying the composition to a substrate and heat-treating the applied layer of the composition.

The Pt film pattern of the present invention is formed on a substrate by the steps of applying the composition to a substrate, pattern-exposing the applied layer of the composition to radiation, washing and removing the unexposed portion of the layer with a solvent, and then heat-treating the patterned layer produced.

When the DMPt(II)TEMDA of formula (1) is used as a coating material for the formation of a Pt film, and since it excels in the stability of the preservation of heat and coating properties and since it exhibits higher activity and greater decomposability than the conventional organic acid salts of Pt, the complex results in the formation of a Pt film having low resistance and a smooth surface by a heat treatment which is performed at such a relatively low temperature as 150° to 500° C.

DMPt(II)TEMDA, upon exposure to radiation such as light, laser radiation, electron beams, or X-rays, easily degrades by dissociation of the Pt—C bond and precipitation of Pt. When the layer of this composition applied on a substrate is exposed to radiation and the unexposed part thereof is washed and removed with a solvent and then the etched layer is heat-treated, a pattern of a Pt film can be easily formed on the substrate.

Generally, the Pt film or the Pt film pattern which is formed from the coated Pt film-forming composition of the invention exhibits a very low sheet resistance of not more than 6.0 $\Omega/cm^2$.

The Ir film or the Ir oxide film-forming composition of the present invention comprises an Ir(I)cyclopentadienyl complex of structural formula (2), (3), or (4) and an organic solvent.

The Ir film is formed on a substrate by the steps of applying the composition to a substrate and then heat-treating the applied layer of the composition in a reducing atmosphere of hydrogen.

The Ir oxide film of this invention is formed on a substrate by the steps of applying the composition to a substrate and then heat-treating the applied layer of the composition in an oxidizing atmosphere.

A pattern based on the Ir film of the present invention is formed on a substrate by the steps of applying the composition to a substrate, pattern-exposing the applied layer of the composition to radiation, washing and removing the unexposed part of the layer with a solvent, and then heat-treating the produced patterned layer in a reducing atmosphere of hydrogen.

A pattern based on the Ir oxide film of the present invention is formed on a substrate by the steps of applying the composition to a substrate, pattern-exposing the applied layer of the composition to radiation, washing and removing the unexposed part of the layer with a solvent, and then heat-treating the produced patterned layer in an oxidizing atmosphere.

When the Ir(I)cyclopentadienyl complex represented by any of the structural formulas (2) through (4) shown above is used as a coating material for the formation of an Ir film, since it excels in stability of preservation of heat and coating properties and since it exhibits higher activity and greater decomposability than a conventional organic acid salt such as iridium octylate, it results in the formation of an Ir film or an Ir oxide film having a low resistance and smooth surface by a heat treatment at a relatively low temperature such as, for example, a heat treatment performed in a reducing atmosphere of hydrogen at a temperature in the range of 150° to 500° C. or a heat treatment performed in an oxidizing atmosphere at a temperature in the range of 350° to 700° C.

The Ir(I)cyclopentadienyl complex, upon exposure to radiation such as light, laser radiation, electron beams, or X-rays, easily degrades by dissociation of the Pt—C bond and deposition of Ir. When the layer of this composition applied on a substrate is exposed to radiation and the unexposed portion thereof is washed and removed with a solvent and then the etched layer is heat-treated, a pattern of the Ir film or the Ir oxide film can be easily formed on the substrate. Generally, the Ir film or the Ir film pattern which is formed of the Ir film-forming composition of the present invention exhibits a very low sheet resistance of not more than 4.0 $\Omega/cm^2$ and the $IrO_2$ film or the $IrO_2$ film pattern which is formed of the Ir oxide film-forming composition of the present invention exhibits a very low sheet resistance of not more than 5.0 $\Omega/cm^2$.

The method of the present invention for the production of a platinum film achieves the formation of a platinum film on a substrate by metalorganic chemical vapor deposition using an organic platinum compound of the following formula [I]. In the method, at least a part of the surface of the substrate employed is formed of an electroconductive material, and the platinum film is formed on the electroconductive material.

(R stands for a hydrogen atom or a methyl group).

An objective of the invention has been to achieve a selective CVD method for the formation of a platinum film. It has been found that when the organic platinum complex of formula [I] is used as the raw material for the formation of a platinum film by the MOCVD method, the platinum film is formed exclusively on the electroconductive material portion of the substrate and not on the remaining insulating material, and that by having a predetermined pattern formed with the electroconductive material on a substrate, the platinum film can be selectively formed on the pattern. This discovery is an important aspect of the present invention.

For the selective formation of the platinum film on the electroconductive material in this invention, the following mechanism is believed to be plausible.

It is known that when hydrogen is used as the reaction gas, the organic platinum complex of formula [I], which serves as the platinum source, readily reacts with the hydrogen in the vapor phase and gives rise to an unsaturated platinum hydride coordination complex. It is also known that this platinum hydride complex itself is a reduced active species having a very high degree of activity. With respect to the main reaction which occurs on the surface of the substrate, the molecules of the produced platinum hydride complex approach the surface of the substrate and adhere through adsorption to the electroconductive material, which possesses a catalytic ability in this reaction because of reciprocal electron transfer and the reciprocal electron transfer is effected at the sites of adsorption. As a result, the platinum hydride complex is reduced and the formation of platinum cores proceeds selectively on the electroconductive material during the first stage of the reaction. Then, around the platinum cores thus formed as centers, the molecules of the remainder of the platinum hydride complex formed in the vapor phase and the molecules of the organic platinum complex of formula [I] react and form platinum particles. These platinum particles are deposited on the cores. It is thought that the reaction which forms the cores on the surface and the reaction between the two species of molecules in the vapor phase proceed cooperatively during the time the active sites exist on the electroconductive material and the formation of a platinum film proceeds which is governed by the rate of supply after the active sites cease to exist.

The Pt film-forming composition of the present invention and the Pt film an the Pt film pattern which are formed by the present composition are described as follows:

The Pt film of the present invention is formed on a substrate by the steps of applying the composition to a substrate and heat-treating the applied layer of the composition.

The Pt film pattern of the present invention is formed on a substrate by the steps of applying the composition to a substrate, exposing the applied layer of the composition through a pattern to radiation, washing and removing the unexposed portion of the layer with a solvent, and then heat-treating the produced patterned layer.

In the Pt film-forming composition of the present invention, DMPt(II)TEMDA is the organic Pt compound. DMPt(II)TMEDA can be synthesized by the method proposed by H. C. Clark and L. E. Manzer (J. Organometallic Chemistry, 59 (1973) 411–428).

The Pt film-forming composition of the present invention can be easily prepared by dissolving the DMPt(II)TMEDA in an organic solvent selected from the group consisting of acetic esters such as ethyl acetate, isopropyl acetate, and butyl acetate; alcohols such as isopropanol (IPA), butanol, and ethanolamine; ethers such as ethylene glycol and dioxane; amines such as N,N,N',N'-tetramethylethylene diamine (TMEDA), and toluene at a concentration in the approximate range of 0.1 to 20% by weight based on the amount of Pt metal in the complex.

The Pt film of the present invention can be easily formed by applying the Pt film-forming composition of the present invention to a substrate of Si, alumina, quartz, AlN, LiNbO$_3$, GaAs, InP, GaN, or polyimide by a spin coating, spray coating, dip coating, or screen printing technique, and then heat-treating the applied layer of the composition at a temperature in the range of 150° to 500° C., preferably 200° to 500° C., for a period in the approximate range of 10 to 60 minutes.

The Pt film pattern of the present invention can be easily formed by applying the Pt film-forming composition in the same manner as described above to the same substrate, exposing the resultant film to radiation as light, laser radiation, electron beam, or X-ray so as to provide a predetermined pattern, washing and removing the unexposed portion of the film thereby effecting development of the film, and heat-treating the developed film under the same conditions as used for the heat treatment for the formation of the Pt film described above.

The formation of a pattern of the Pt film may be accomplished by using a mask, which defines a pattern over an applied film of the composition and then exposing the assembly to radiation or by exposing the applied composition to a laser beam which is scanned over the applied film in a given pattern.

For the development which follows exposure, a solution containing hydrochloric acid, nitric acid, or sulfuric acid at a concentration in the range of 0.1 to 20% by weight in IPA or ethyl oxobutanoate can be used as a solvent.

The Pt film-forming composition of the present invention may further comprise an alkoxide such as a methoxide, ethoxide, isopropoxide, or butoxide of at least one metal selected from the group consisting of Si, B, P, Bi, Ti, Zr, V, Nb, Ta, Ge, and Pb; an organic acid salt such as an octylate or 2-ethyl acetate of the metal mentioned above, or a metal chelate compound such as an acetylacetonate salt. The incorporation of the metal compound in the composition can enhance the adhesiveness of the formed Pt film or Pt film pattern which is formed on the substrate and the mechanical strength of these films. When the composition contains the metal compound, the heat treatment during the formation of the Pt film or Pt film pattern must be performed at a temperature of not less than 500° C., preferably in the range of 500° to 700° C.

As examples of the metal compound which can be incorporated effectively in the Pt film-forming composition, TEOS (ethyl silicate), TEOS hydrolyzate, B(OC$_3$H$_5$)$_3$, PO(OC$_2$H$_5$)$_3$, Bi octylate, Ti(O-i-C$_3$H$_7$)$_4$, Zr(OC$_4$H$_9$)$_4$, VO(O-i-C$_3$H$_7$)$_3$, Nb(OC$_2$H$_5$)$_5$, Ta(OC$_2$H$_5$)$_5$, Ge(OC$_2$H$_5$)$_4$, and Pb octylate may be used. The content of the metal compound in the composition is properly in the range of 0.1 to 5.0% by weight based on the oxide of the metal.

The Ir film or the Ir oxide film-forming composition of the present invention and the Ir film, the Ir oxide film, the Ir film pattern, and the Ir oxide film pattern which are formed of an embodiment of the composition are described infra.

The Ir(I)cyclopentadienyl complex which is used as an organic Ir compound in the preparation of the Ir film or the Ir oxide film-forming composition of this invention is a 1,5-cyclooctadiene-Ir(I)cyclopentadienyl complex ("CpIrCOD"), represented by structural formula (2), a 1,3,5-cyclooctatriene-Ir(I)cyclopentadienyl complex ("CpIrCOT") represented by structural formula (3), or a 1,3,5,7-cyclooctatetraene-Ir(I)cyclopentadienyl complex ("CpIrCOTE") represented by structural formula (4).

In the Ir(I)cyclopentadienyl complexes mentioned above, CpIrCOD can be synthesized by the method proposed by S. D. Robinson et al. (J. Chem. Soc., 1965, 4997), CpIrCOT by the method proposed by J. Evance et al (J. Chem. Soc., Dalton Trans., 1972, 2668), and CpIrCOTE by the method proposed by H. Yamazaki et al. (Bull. Chem. Soc. Jpn., 1971, 44,582), for example.

In the present invention, the Ir(I)cyclopentadienyl complexes may be used either singly or in the form of a mixture of two or more members.

The Ir film or the Ir oxide film-forming composition of the present invention can be easily prepared by dissolving the Ir(I)cyclopentadienyl complex in an organic solvent selected from the group consisting of acetic esters such as ethyl acetate, isopropyl acetate, and butyl acetate; alcohols such as isopropanol (IPA), butanol, and ethanol amine; ethers such as ethylene glycol and dioxane; amines such as N,N,N',N'-tetramethylethylene diamine (TMEDA), and toluene at a concentration in the approximate range of 0.1 to 30% by weight based on the amount of Ir metal in the complex.

The Ir film of the present invention can be easily formed by applying the Ir film or the Ir oxide film-forming composition of the invention to a substrate of Si, SiO$_2$, GaAs, InP, GaN, Al$_2$O$_3$, AlN, or polyimide by a spin coating, spray coating, dip coating, or screen printing technique, and then heat-treating the applied layer of the composition in a reducing atmosphere of hydrogen at a temperature in the range of 150° to 500° C., preferably 200° to 450° C., for a period in the approximate range of 1 to 30 minutes.

The Ir oxide film of the invention can be easily formed by applying the Ir film or the Ir oxide film-forming composition of the invention to a substrate in the same manner as described above and then heat-treating the applied layer of the composition in an oxidizing atmosphere at a temperature in the range of 350° to 700° C., preferably 400° to 600° C., for a period in the approximate range of 5 to 30 minutes.

The Ir film pattern of the present invention can be easily formed by applying the Ir film or the Ir oxide film-forming composition of the invention as described above to the same substrate, exposing the resultant film to radiation such as light, laser radiation, electron beams, or X-rays in a predetermined pattern, washing and removing the unexposed portion of the film thereby effecting development of the pattern, and heat-treating the developed film in a reducing atmosphere of hydrogen under the same conditions as used for the heat treatment for the formation of the Ir film mentioned above.

The Ir oxide film pattern of the present invention can be easily formed by applying the Ir film or the Ir oxide film-forming composition of the invention in the same manner as described above to a substrate, pattern-exposing the resultant film to radiation followed by development, and heat-treating the developed film in an oxidizing atmosphere under the same conditions as used for the heat treatment for the formation of the Ir oxide film mentioned above.

After formation of the Ir film or Ir oxide film, a pattern is formed in the metal or oxide film by exposure of the film through a master pattern or by exposure of the film to a scanning laser beam, which scans the film in a given pattern.

For the development which follows the exposure, a solution containing hydrochloric acid, nitric acid, sulfuric acid, or hydrofluoric acid at a concentration in the range of 0.1 to 10% by weight in IPA, butanol, or dioxane can be used as a solvent.

The method of the present invention for the production of a platinum film is now described with reference to the accompanying drawings.

FIG. 1 and FIG. 2 are cross sections of electroconductive devices of the present invention which have a patterned Pt film prepared by method embodiments of the present invention.

The organic platinum compound which is used as the raw material for film formation in the present invention is a (cyclopentadienyl) trimethylplatinum (IV) (Cp)TMPt), wherein R in formula (I) is hydrogen or a (methylcyclopentadienyl) trimethylplatinum (IV), Me(Cp) PtTM) wherein R in formula (I) is methyl.

These organic platinum complexes can be synthesized, for example, by synthesizing iodine trimethylplatinum (IV) [(CH$_3$)$_3$PtI], which has a methyl group attached to the platinum atom by the reaction of potassium chloroplatinate (IV) (K$_2$PtCl$_6$) (commercially available) with a Grignard reagent, and then subsequently directly reacting the methyl compound [(CH$_3$)$_3$PtI] in a non-aqueous medium with the sodium salt of cyclopentadiene or methyl cyclopentadiene.

The electroconductive material which is used for selective formation of a platinum film with an organic platinum complex as mentioned above, is for example, an element of Group 4A, Group 5A, or Group 6A of the Periodic Table of Chemical Elements. These elements include titanium (Ti), tantalum (Ta), zirconium (Zr), tungsten (W), iridium (Ir), ruthenium (Ru), and silicon (Si), as well as the nitrides of these metals. Although all these electroconductive materials are capable of satisfactorily implementing selective formation of a platinum film, the metals of Group 4A or the nitrides thereof are particularly selectively effective in film formation.

Embodiments of the selective CVD method of forming a patterned platinum film according to the present invention, noted as methods (1) or (2), include the following:

(1) A method which comprises forming a pattern made of an electroconductive material on a substrate whose surface is formed of an insulating material and superposing a platinum film on the electroconductive pattern.

(2) A method which comprises forming a patterned coating film made of an insulating material on a substrate whose surface is formed of an electroconductive material and superposing a platinum film on the exposed electroconductive material which is not covered with insulating material.

Figure 1A:
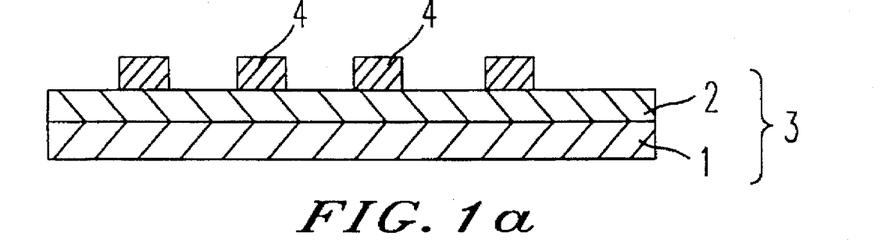
FIG. 1(a) shows a substrate having a patterned electroconductive material layer produced by CVD method embodiment (1)
Figure 1B:
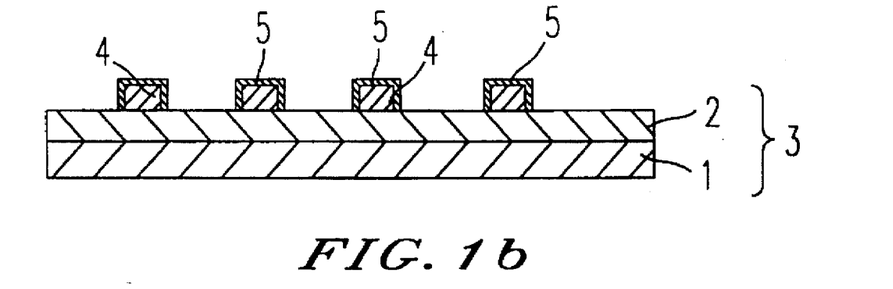
FIG. 1(b) shows the patterned substrate of FIG. 1(a) provided with a layer of Pt film by method embodiment (1)

In the case of method (1) above, a substrate 3 obtained by subjecting the surface of a silicon substrate to a thermal oxidizing treatment, thereby forming a SiO$_2$ surface layer 2 on the surface of an Si basal layer 1 (hereinafter a "thermal SiO$_2$ substrate"), is shown in FIG. 1(a). The electroconductive material mentioned above is vapor deposited on the surface of the substrate 3 by a film forming method such as a sputtering method and the resultant vapor deposited film is etched into a pattern of a desired shape to produce a pattern 4 of the electroconductive material. When the organic platinum complex of formula [I] is deposited by the MOCVD method in the form of a film as practiced normally on the substrate, no platinum film is formed on the exposed portion of the SiO$_2$ surface layer 2 and a platinum film 5 is formed exclusively on pattern 4 of the electroconductive material thereby forming a platinum film pattern as shown in FIG. 1(b). The formation of the sputtered film of the electroconductive material and the formation of the platinum film are carried out under vacuum throughout the entire process.

In the method of embodiment (1), a superposed substrate having the surface of the thermal SiO$_2$ substrate mentioned above formed of such an insulating material as Si$_3$N$_4$, SiO, or SiN can be used as the substrate.

Figure 2A:
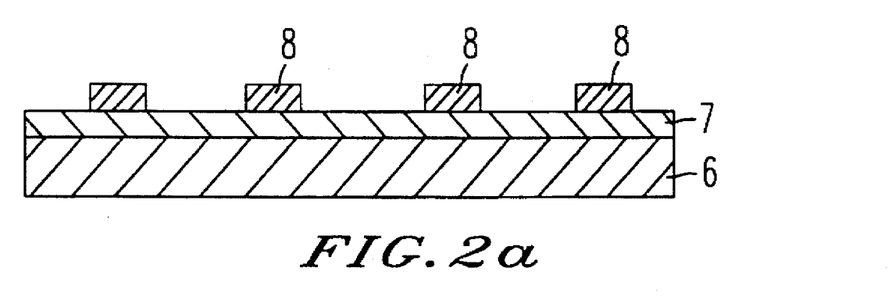
FIG. 2(a) shows a substrate having a patterned insulating layer over a complete layer of electroconductive material which is used in method embodiment (2) of the invention.
Figure 2B:
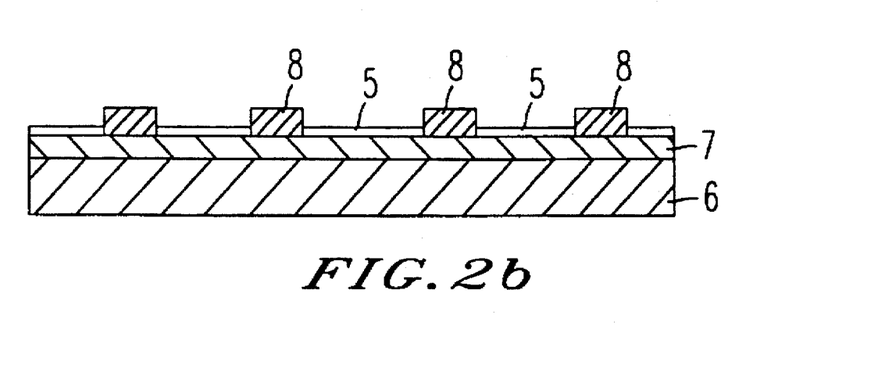
FIG. 2(b) shows the substrate of FIG. 2(a) coated with a Pt film by the CVD method.

In contrast, in method (2), a coating film 7 of an electroconductive material is formed on a substrate 6 such as of silicon and a coating film 8 of an insulating material such as, for example, Si$_3$N$_4$ is so formed on the coating film 7 of an electroconductive material as to cover a portion of the coating film except for the desired pattern portion as shown in FIG. 2(a). When the organic platinum complex of formula [I] mentioned above is deposited by the MOCVD method in the form of a film as practiced normally on the substrate, no platinum film is formed on the patterned coated film 8 of the insulating material and a platinum film 5 is formed exclusively on the exposed pattern of coated film 7 of the electroconductive material thereby forming a platinum film pattern as shown in FIG. 2(b).

The selective formation of the platinum film exclusively on the patterned electroconductive material of the substrate in this invention requires that the conditions for film formation by the MOCVD method be controlled. In order to realize the selective film formation perfectly, it is appropriate to set the temperature of the substrate during the course of film formation in the range of 180° to 220° C. and use hydrogen as the reaction gas, for example. If the temperature of the substrate is higher than 220° C., the selective formation of the platinum film will not be attained and the platinum film will form on a portion of the insulating material of the substrate. Since the temperature of the substrate is variable with the flow volume of the reaction gas, the degree of vacuum, and other conditions of film formation, there are cases in which the selective formation of the platinum film will be attained at a temperature within the range of 180° to 220° C.

If the atmosphere for film formation contains components which contain a hydroxyl group or if the substrate has hydroxyl groups on its surface, selective film formation will not be perfectly attained at times. For selective formation of the platinum film, therefore, it is advantageous to conduct film formation in the absence of steam and, after the formation of a pattern of a coating film of electroconductive material on the substrate, to subject the substrate to a vacuum heat treatment in a reaction furnace of the MOCVD method and effect thorough removal of residual hydroxyl groups from the substrate. Appropriately, this vacuum heat treatment is carried out in an atmosphere of $N_2$ or Ar under a reduced pressure in the range of $10^{-4}$ to $10^{-6}$ torr at a temperature in the range of 200° to 500° C. for a period in the range of 60 to 120 minutes.

Having generally described this invention, a further understanding can be obtained by reference to certain specific examples which are provided herein for purposes of illustration only and are not intended to be limiting unless otherwise specified.

EXAMPLE 1

Synthesis of DMPt(II)TMEDA

DMPt(II)TMEDA was synthesized by the method disclosed by H. C. Clark and L. E. Manzer (J. Organometallic Chemistry, 59 (1973) 411–428). First, a dimethyl Pt(II) cyclooctadiene complex represented by structural formula (5) was synthesized, dissolved in TMEDA, and subjected to a thermal reaction. After the reaction, the reaction mixture was distilled under reduced pressure to remove excess TMEDA and cyclooctadiene by vaporization to obtain DMPt(II)TMEDA.

(5)

Preparation of Pt film-forming composition

A Pt film-forming composition was prepared by dissolving the produced DMPt(II)TMEDA in various solvents indicated in Table 1 at a ratio of 10% by weight as Pt concentration.

Formation of Pt film

The Pt film-forming composition thus obtained was applied to a Si (110) substrate by a spin coating technique and then fired at a temperature as shown in Table 1 for 30 minutes.

In all the test runs involved herein, smooth Pt films could be formed. When the films consequently obtained were tested for sheet resistance, they were found to exhibit low degrees of resistance as shown in Table 1.

The Pt films were tested for adhesiveness by a peel test with an adhesive tape and for mechanical strength by the pencil hardness test. The results are shown in Table 1. Adhesiveness was rated on a three-point scale as fair<good<excellent.

TABLE 1

| No. | Solvent | Temperature of heat treatment (°C.) | Sheet resistance ($\Omega$/cm$^2$) | Peel test with adhesive tape (pencil hardness test) |
|---|---|---|---|---|
| 1 | Toluene | 150 | 4.2 | Fair (1H) |
| 2 | Toluene | 350 | 2.2 | Good (3H) |
| 3 | Butyl acetate | 250 | 2.6 | Good (2H) |
| 4 | Butyl acetate | 350 | 2.2 | Good (3H) |
| 5 | TMEDA | 200 | 2.8 | Good (2H) |
| 6 | TMEDA | 400 | 1.5 | Good (3H) |
| 7 | Diethanol amine | 250 | 2.9 | Good (2H) |
| 8 | Diethanol amine | 350 | 2.0 | Good (3H) |

EXAMPLE 2

In Run Nos. 1 to 8 of Example 1, a relevant Pt film-forming composition was applied to a substrate. Each of the applied films of the composition was then treated in the same manner as described in Example 1, except that the applied film was exposed to XeCl light (308 nm) which was passed through a patterned mask to induce precipitation of Pt, followed by removing the unexposed portion of the film with an IPA 10 wt. % hydrochloric acid solution and heat-treating the resultant patterned film. Thus, a satisfactory Pt film pattern was formed for each of the samples.

EXAMPLE 3

The procedure of Example 2 was followed, except that exposure was effected by scanning with an Ar ion laser beam ($1 \sim 9 \times 10^5$ W/cm$^2$) in place of exposure to the XeCl light passed through a patterned mask, with the result that a satisfactory Pt film pattern could be formed for each of the samples.

EXAMPLE 4

Various Pt film-forming compositions were prepared by dissolving DMPt(II)TMEDA in a different solvents are shown in Table 2, each solution providing a Pt concentration of 10% by weight. Thereafter, various metal compounds also shown in Table 2 were added to the resultant solutions in various concentrations in terms of the metal oxide as shown in Table 2.

The Pt film-forming compositions were applied to a various substrates as shown in Table 2 by the spin coating technique and then heat-treated at various temperatures as shown in Table 2.

As a result, smooth Pt films could be formed for the samples. The Pt films thus obtained were tested for sheet resistance, and they were found to have low degrees of resistance as shown in Table 2.

The Pt films were tested for adhesiveness by a peel test with an adhesive tape and for mechanical strength by the pencil hardness test. The results are shown in Table 2.

It can be observed from Table 2, that the use of metal compounds such as of Si, Bi, Ti, V, and B allowed the preparation of Pt films of improved adhesiveness and mechanical strength.

TABLE 2

| No. | Solvent | Metal Compound Kind | Concentration as reduced to metal oxide (% by weight) | Material of substrate | Temperature of heat treatment (°C.) | Sheet resistance ($\Omega/cm^2$) | Peel test with adhesive tape (pencil hardness test) |
| --- | --- | --- | --- | --- | --- | --- | --- |
| 9 | Toluene | TEOS hydrolyzate | $SiO_2$: 1 | Alumina | 700 | 2.2 | Excellent(4H) |
| 10 | Toluene | TEOS hydrolyzate Bi octylate | $SiO_2$: 1 $Bi_2O_3$: 0.3 | Alumina | 500 | 5.2 | Good(3H) |
| 11 | Butyl acetate | $Ti(O-i-C_3H_7)_4$ | $TiO_2$: 1 | Quartz | 600 | 3.6 | Excellent(3H) |
| 12 | Butyl acetate | TEOS hydrolyzate | $SiO_2$: 1 | AlN | 550 | 3.9 | Good(2H) |
| 13 | Butyl acetate | TEOS hydrolyzate Bi octylate | $SiO_2$: 1 $Bi_2O_3$: 1 | Alumina | 700 | 2.2 | Excellent(3H) |
| 14 | Diethanol amine | $Ti(O-i-C_3H_7)_4$ | $TiO_2$: 1 | Quartz | 700 | 1.6 | Excellent(3H) |
| 15 | Diethanol amine | TEOS hydrolyzate Bi octylate | $SiO_2$: 1 $Bi_2O_3$: 0.3 | AlN | 550 | 3.6 | Good(2H) |
| 16 | Diethanol amine | $Ti(O-i-C_3H_7)_4$ | $TiO_2$: 1 | Alumina | 700 | 1.6 | Excellent(4H) |
| 17 | TMEDA | TEOS hydrolyzate | $SiO_2$: 1 | Quartz | 700 | 2.6 | Excellent(3H) |
| 18 | TMEDA | TEOS hydrolyzate $VO(O-i-C_3H_7)_3$ | $SiO_2$: 1 $V_2O_2$: 0.3 | AlN | 550 | 3.0 | Good(1H) |
| 19 | TMEDA | TEOS hydrolyzate Bi 2-ethyl butyrate | $SiO_2$: 1 $Bi_2O_3$: 0.5 | Alumina | 700 | 2.3 | Excellent(3H) |

EXAMPLE 5

In Run Nos. 9 to 19 of Example 4, a relevant Pt film-forming composition was applied to a substrate. Each of the film coated samples was then treated in the same manner as described in Example 4, except that the applied film was exposed to XeCl light (308 nm) which passes through a patterned mask to induce precipitation of Pt, followed by removal of the unexposed portion of the film with an IPA 10 wt. % hydrochloric acid solution and heat-treating the resultant patterned film. Thus, a satisfactory patterned Pt film was formed for each of the samples.

EXAMPLE 6

The procedure of Example 5 was followed, except that radiation exposure was accomplished with a scanning Ar ion laser beam ($1\sim9\times10^5$ W/cm$^2$), instead of the exposure to XeCl light passed through a patterned mask, with the result that a satisfactory Pt film pattern could be formed for each of the samples.

It is clearly noted from the examples cited above that the Pt film-forming compositions of the present invention excel in stability of heat preservation and coating properties and exhibit relatively high decomposability and, consequently, permit Pt films of low resistance and smooth surface to form easily upon a heat treatment at a relatively low temperature. Further, since the compositions easily result in precipitation of Pt upon exposure to radiation, patterned Pt films can be easily formed on a substrate by the steps of exposing a Pt film to radiation, developing the exposed Pt film, and heat-treating the developed Pt film.

Pt films formed with the Pt film-forming compositions of the present invention are very useful as electrode materials of various types, because they have smooth surfaces and low resistance. Particularly, the patterned film of the present has a significant commercial advantage in that circuit patterns can be easily and efficiently formed with high efficiency.

EXAMPLE 7

Various Ir(I)cyclopentadienyl complexes shown in Table 3 were dissolved in various solvents shown in Table 3 in an amount of 7% by weight, Ir concentration, from which Ir film or Ir oxide film-forming compositions could be prepared.

An Ir film or the Ir oxide film-forming composition thus obtained was applied to a Si (110) substrate by the spin coating technique (at 1000 rps for five seconds or at 300 rps for 15 seconds) and then fired in an atmosphere of $H_2$—Ar ($H_2$:Ar=2:8 by volumetric ratio) or in an atmosphere of $O_2$ at the various temperatures shown in Table 3 for 30 minutes.

In all the test runs involved, smooth Ir films or $IrO_2$ films could be formed. When the films were tested for sheet resistance, they were found to have low degrees of resistance as shown in Table 3.

TABLE 3

| No. | Ir(I) cyclopentadienyl complex | Kind of solvent | Conditions of heat treatment Temperature (°C.) | Ambience | Composition of film | Sheet resistance ($\Omega/cm^2$) |
| --- | --- | --- | --- | --- | --- | --- |
| 20 | CPIrCOD | Toluene | 150 | $H_2$—Ar | Ir | 2.5 |
| 21 | CPIrCOD | Butyl acetate | 250 | $H_2$—Ar | Ir | 0.9 |
| 22 | CpIrCOD | TMEDA | 250 | $H_2$—Ar | Ir | 0.9 |
| 23 | CpIrCOT | Butyl acetate | 250 | $H_2$—Ar | Ir | 1.3 |
| 24 | CpIrCOT | TMEDA | 300 | $H_2$—Ar | Ir | 0.8 |
| 25 | CpIrCOT | Diethanol amine | 300 | $H_2$—Ar | Ir | 0.8 |
| 26 | CpIrCOTE | TMEDA | 250 | $H_2$—Ar | Ir | 3.5 |
| 27 | CpIrCOTE | TMEDA | 250 | $H_2$—Ar | Ir | 3.5 |
| 28 | CpIrCOTE | TMEDA | 300 | $H_2$—Ar | Ir | 3.6 |

TABLE 3-continued

| Ir(I) No. | cyclo-pentadienyl complex | Kind of solvent | Conditions of heat treatment Temperature (°C.) | Ambience | Composition of film | Sheet resistance (Ω/cm²) |
|---|---|---|---|---|---|---|
| 29 | CPIrCOD | Toluene | 350 | O₂ | IrO₂ | 0.7 |
| 30 | CpIrCOD | Butyl acetate | 400 | O₂ | IrO₂ | 0.7 |
| 31 | CpIrCOD | TMEDA | 500 | O₂ | IrO₂ | 0.7 |
| 32 | CpIrCOT | Butyl acetate | 350 | O₂ | IrO₂ | 0.7 |
| 33 | CPIrCOT | TMEDA | 400 | O₂ | IrO₂ | 0.7 |
| 34 | CpIrCOT | Diethanol amine | 450 | O₂ | IrO₂ | 1.1 |
| 35 | CPIrCOTE | TMEDA | 350 | O₂ | IrO₂ | 1.1 |
| 36 | CpIrCOTE | TMEDA | 500 | O₂ | IrO₂ | 0.6 |
| 37 | CpIrCOTE | TMEDA | 550 | O₂ | IrO₂ | 0.6 |

EXAMPLE 8

In Run Nos. 20 to 37 of Example 7, an Ir film or Ir oxide film-forming composition was applied to a substrate. Each of the applied films was then treated in the same manner as described in Example 1, except that each applied film was exposed to light XeCl (308 nm, 30 Hz, 1 mJ) through a patterned mask to induce precipitation of Pt, followed by removing the unexposed portion of the film with an IPA 10 wt. % hydrochloric acid solution and heat-treating the patterned film consequently obtained. Thus, a satisfactory Pt film pattern or IrO₂ film pattern was formed in each case.

EXAMPLE 9

The procedure of Example 8 was followed, except that exposure was effected by scanning with an Ar ion laser beam (CW output 10 W, 515 nm) instead of exposure to XeCl light passed through the patterned mask, with the result that a satisfactory Pt film or IrO₂ film pattern could be formed for each sample.

EXAMPLE 10

The procedure of Example 9 was followed, except that exposure was carried out with an electron beam of a beam current of 5 μA in the place of the Ar ion laser light, with the result that a satisfactory Ir film pattern or IrO₂ film pattern could be formed.

Comparative Example 1

An Ir film was formed in the same manner as the film in Run No. 20 of Example 7, except that iridium octylate was used in place of CpIrCOD and the temperature of the heat treatment was changed to 250° C. The Ir film produced showed a high sheet resistance of 23 Ω·cm².

Comparative Example 2

An IrO₂ film was formed in the same manner as the film in Comparative Example 1, except that the heat treatment was carried out in an atmosphere of oxygen at 400° C. instead. The IrO₂ film produced showed a high sheet resistance of 74 Ω/cm².

Comparative Example 3

No Ir film pattern could be formed on a substrate when a solution containing iridium octylate was applied to a Si substrate in the same manner as described in Comparative Example 1 and the applied layer of the solution was subjected to exposure and development in the same manner as described in Example 8.

It can be clearly observed from the examples above that the Ir film or the Ir oxide film-forming compositions of the present invention excel in stability of heat preservation and coating properties and exhibit relatively high decomposability and, permit Ir films or Ir oxide films of low resistance and smooth surface to be easily formed by a heat treatment performed at a relatively low temperature. Further, since Ir readily precipitates from the compositions upon exposure to radiation, Ir film or Ir oxide film patterns can be easily formed on a substrate by the steps of exposing an Ir film to radiation, developing the exposed Ir film, and heat-treating the developed Ir film.

The Ir films or the Ir oxide films which are formed from the Ir film or Ir oxide film-forming compositions of the present invention are very useful as electrode materials of varying types because they have smooth surfaces and low resistance. Particularly, the Ir film or the Ir oxide film patterns of the present invention have a significant commercial advantage of permitting a circuit pattern to be easily and efficiently formed with high efficiency.

EXAMPLE 11

By the use of an apparatus as shown in FIG. 3, selective formation of a platinum film was effected by the method by which the structure shown in FIG. 1 using (Cp)PtTM was produced.

As the substrate, a thermal SiO₂ substrate having an area of 25 mm on which a thin film (5 nm thickness) of an eletroconductive material, as shown in Table 4, was deposited by the sputtering method, followed by etching the thin film to form a pattern therein.

For film formation, the substrate was first set in place in the reaction furnace 7 and then subjected to a vacuum heat treatment (under a reduced pressure of $10^{-6}$ torr at 500° C. in an atmosphere of N₂ for 60 minutes). Subsequently, a platinum film of (Cp)PtTM was formed on the substrate under the following conditions.

Substrate temperature: 200° C.
Vaporizing temperature: 30° C.
Pressure: 10 torr
Flow volume of carrier gas: 50 cc/min. of Ar
Flow volume of reaction gas: 50 cc/min. of H₂
Duration of film formation: 30 minutes The platinum films consequently obtained were tested for selectivity, (selectivity is determined on a scale by which a sample having a platinum film formed exclusively on a pattern of electroconductive material is rated as "presence" of selectivity and a sample having a portion of the platinum film formed on a portion outside the pattern of electroconductive material as "absence" of selectivity.), film thickness, particle diameter, and speed of film formation. The results are shown in Table 4.

The platinum films were tested for adhesive force by the following method. The results are shown in Table 4.

Test for Adhesive Force (Crosscut Test)

By the use of a crosscut guide (having a total width of 1 cm) having parallel grooves of a width of 1 mm incised therein in one direction, a square of 1 cm was incised in the surface of a platinum film deposited on the substrate by depressing the crosscut guide twice in perpendicular directions into the surface. Since the crosscut guide contained grooves of a width of 1 mm, a total of 100 squares of 1 mm existed within the square. An adhesive tape was applied to the surface of the platinum film having 100 square grooves and then peeled from the surface. The number, N, of squares which did not adhere to the adhesive tape but remained on the substrate was counted. The adhesive force was rated by the designation (N/100). The adhesive force decreases in proportion to decreases in the numerical value of N.

TABLE 4

| No. | Electro-conductive material | Selec-tivity | Film thick-ness (μm) | Particle diameter (nm) | Rate of film formation (μm/hour) | Results of test for adhesive force |
|---|---|---|---|---|---|---|
| 38 | Ti | Presence | 0.15 | 3.2 | 0.30 | 95/100 |
| 39 | Ta | Presence | 0.18 | 3.1 | 0.35 | 92/100 |
| 40 | TiN | Presence | 0.20 | 3.0 | 0.40 | 90/100 |
| 41 | Ir | Presence | 0.19 | 2.9 | 0.38 | 95/100 |
| 42 | W | Presence | 0.18 | 2.95 | 0.35 | 100/100 |
| 43 | Ru | Presence | 0.16 | 3.0 | 0.32 | 100/100 |
| 44 | Zr | Presence | 0.19 | 3.1 | 0.38 | 95/100 |
| 45 | ZrN | Presence | 0.20 | 3.1 | 0.4 | 95/100 |
| 46 | Si | Presence | 0.19 | 2.9 | 0.38 | 90/100 |

Comparative Example 4

Platinum films were formed in the same manner as described in Run Nos. 38 to 46 of Example 11, except that a mixed gas formed by adding water to Ar at a ratio of 2% or 5% (partial pressure) was used as the carrier gas. All of the produced platinum films showed no selectivity.

In the platinum films produced, the film thicknesses were in the range of 0.13 to 0.20 μm, the particle diameters in the range of 3.2 to 3.4 nm, and the rates of film formation in the range of 0.3 to 0.4 μm/hour. The results of test for adhesive force performed in the same manner as described in Example 11 were in the range of 60/100 to 70/100, indicating that the platinum films possessed poor adhesive force.

Comparative Example 5

Platinum films were formed using electroconductive materials/substrates in Run Nos. 38 to 46 of Example 11 (Nos. 47 to 55 in Table 5) and a thermal SiO$_2$ substrate (No. 56 in Table 5), in the same manner as described in Example 11, except that the substrate temperature was changed to 250° C. or 400° C. The produced platinum films were tested for selectivity, film thickness, particle diameter and rate of film formation. The results are shown in Table 5. These results were substantially equal when the substrate temperature was 250° C. and when it was 400° C.

TABLE 5

| No. | Electro-conductive material/-substrate | Selec-tivity | Film thickness (μm) | Particle diameter (nm) | Rate of film formation (μm/hour) |
|---|---|---|---|---|---|
| 47 | Ti/SiO$_2$ | Absence | 0.25 | 3.5 | 0.50 |
| 48 | Ta/SiO$_2$ | Absence | 0.23 | 3.8 | 0.45 |
| 49 | TiN/SiO$_2$ | Absence | 0.26 | 3.2 | 0.51 |
| 50 | Ir/SiO$_2$ | Absence | 0.26 | 3.6 | 0.52 |
| 51 | W/SiO$_2$ | Absence | 0.25 | 3.5 | 0.49 |
| 52 | Ru/SiO$_2$ | Absence | 0.26 | 3.1 | 0.51 |
| 53 | Zr/SiO$_2$ | Absence | 0.25 | 3.3 | 0.50 |

TABLE 5-continued

| No. | Electro-conductive material/-substrate | Selec-tivity | Film thickness (μm) | Particle diameter (nm) | Rate of film formation (μm/hour) |
|---|---|---|---|---|---|
| 54 | ZrN/SiO$_2$ | Absence | 0.26 | 3.7 | 0.52 |
| 55 | Si/SiO$_2$ | Absence | 0.24 | 3.8 | 0.48 |
| 56 | SiO$_2$ | Absence | 0.27 | 3.9 | 0.53 |

EXAMPLE 12

Platinum films were formed in the same manner as described in Run Nos. 38 to 46 of Example 11, except that Me(Cp)PtTM was used in place of (Cp)PtTM. The films produced were tested in the same manner as described in Example 11. The results are shown in Table 6.

TABLE 6

| No. | Electro-conductive material | Selec-tivity | Film thick-ness (μm) | Particle diameter (nm) | Rate of film formation (μm/hour) | Results of test for adhesive force |
|---|---|---|---|---|---|---|
| 57 | Ti | Presence | 0.18 | 2.9 | 0.36 | 95/100 |
| 58 | Ta | Presence | 0.21 | 3.0 | 0.42 | 98/100 |
| 59 | TiN | Presence | 0.22 | 3.0 | 0.44 | 93/100 |
| 60 | Ir | Presence | 0.22 | 2.9 | 0.44 | 100/100 |
| 61 | W | Presence | 0.19 | 2.9 | 0.38 | 100/100 |
| 62 | Ru | Presence | 0.19 | 3.1 | 0.38 | 100/100 |
| 63 | Zr | Presence | 0.20 | 2.9 | 0.40 | 98/100 |
| 64 | ZrN | Presence | 0.21 | 3.0 | 0.42 | 95/100 |
| 65 | Si | Presence | 0.21 | 2.9 | 0.42 | 90/100 |

Comparative Example 6

Platinum films were formed in the same manner as described in Run Nos. 57 to 65 of Example 12, except that a mixed gas obtained by adding water to Ar at a ratio of 2% or 5% (partial pressure) was used as the carrier gas. None of the produced platinum films showed selectivity.

In the platinum films produced, the film thicknesses were in the range of 0.15 to 0.20 μm, the particle diameters in the range of 2.9 to 3.0 nm, and the rates of film formation in the range of 0.3 to 0.4 μm/hour. The results of the tests for adhesive force performed in the same manner as described in Example 11 were in the range of 60/100 to 70/100, indicating that the platinum films possessed poor adhesive force.

Comparative Example 7

Platinum films were formed using electroconductive materials 4/substrate 3 in Run Nos. 57 to 65 of Example 12, and a thermal SiO$_2$ substrate 3, in the same manner as described in Example 12, except that the substrate temperature was changed to 250° C. or 400° C. The platinum films produced were tested for selectivity, film thickness, particle diameter and rate of film formation. The results are shown in Table 7. These results were practically equal when the substrate temperature was 250° C. and when it was 400° C.

TABLE 7

| No. | Electro-conductive material/-substrate | Selectivity | Film Thickness (μm) | Particle diameter (nm) | Rate of film formation (μm/hour) |
|---|---|---|---|---|---|
| 66 | Ti/SiO$_2$ | Absence | 0.29 | 3.3 | 0.58 |
| 67 | Ta/SiO$_2$ | Absence | 0.30 | 3.5 | 0.60 |
| 68 | TiN/SiO$_2$ | Absence | 0.30 | 3.2 | 0.60 |
| 69 | Ir/SiO$_2$ | Absence | 0.30 | 3.6 | 0.60 |
| 70 | W/SiO$_2$ | Absence | 0.31 | 3.3 | 0.62 |
| 71 | Ru/SiO$_2$ | Absence | 0.32 | 3.4 | 0.63 |
| 72 | Zr/SiO$_2$ | Absence | 0.33 | 3.3 | 0.66 |
| 73 | ZrN/SiO$_2$ | Absence | 0.31 | 3.7 | 0.62 |
| 74 | Si/SiO$_2$ | Absence | 0.32 | 3.8 | 0.64 |
| 75 | SiO$_2$ | Absence | 0.31 | 3.9 | 0.62 |

EXAMPLE 13

Selective formation of platinum films was carried out in the same manner as described in Example 11, except that substrates were used in which various electroconductive coating films of tantalum or titanium were superposed on a Si substrate and the coating film was partially covered with an insulating film according to FIG. 2. The platinum films could be formed only on the exposed parts of the electroconductive coating films of tantalum or titanium.

The results of the examples and the comparative examples above clearly imply the following conclusions.

In Examples 11 and 12, platinum films were formed only on the patterns of an electroconductive material superposed on thermal SiO$_2$ substrates and no platinum film was formed on the remaining SiO$_2$ film parts of the substrates, indicating satisfactory parts of the selectivity of film formation. In Example 13, platinum films were formed only on the exposed portions of the electroconductive material and no platinum film was formed on insulating coating films of Si$_3$N$_4$, for example, indicating perfect selectivity of film formation.

By contrast, Comparative Examples 4 and 6 demonstrate that no selectivity was obtained when the carrier gas contained water. These results are logically explained by the supposition that the hydroxyl groups of the entrained water are adsorbed on the patterned electroconductive material and on the SiO$_2$ film. These groups promote the formation of platinum cores, thereby resulting in no selectivity. When the substrate temperature was set at 250° C. or at 400° C. as in Comparative Examples 5 and 7, no selectivity in the formation of platinum films is observed and the formation of a platinum film was observed on the SiO$_2$ film, as well as on the pattern of an electroconductive material. These results indicate that no selectivity of film formation is observed when the temperature of the substrate is higher than the temperatures of Examples 11 and 12 and the other conditions are the same, even in the case when the platinum compound, as the raw material, is decomposed on the substrate.

As described above, the method of the present invention easily provides platinum films characterized by excellent flatness of surface. Further, the films are efficiently formed and exhibit high adhesiveness to substrates when prepared by the MOCVD technique.

Particularly in the formation of a platinum film, selective formation of the platinum film on a patterned film of an electroconductive material obviates the heretofore imperative necessity for fine work in forming the platinum film, such as by dry etching, and permits simplification of the process of production and reduction of the time required for production. The present invention also further precludes the necessity of harsh ion milling work involved in the dry etching, which may possibly inflict damage on dielectric films which are interposed between the platinum films.

Having now fully described the invention, it will be apparent to one of ordinary skill in the art that many changes and modifications can be made thereto without departing from the spirit or scope of the invention as set forth herein.

What is claimed as new and desired to be secured by Letter Patent of the United States is:

1. A Pt film-forming composition comprising:

a dimethyl Pt(II) (N,N,N',N'-tetramethylethylenediamine complex of formula (1), an organic solvent, and an alkoxide of at least one metal selected from the group consisting of Si, B, P, Bi, Ti, Zr, V, Nb, Ta, Ge, and Pb or an acid salt of said metal.

2. The Pt film-forming composition according to claim 1, wherein said alkoxide of said metal or said organic acid salt of said metal is present at a concentration in the range of 0.1 to 5.0% by weight based on the oxide of the metal.

* * * * *